United States Patent
Bolmsjö et al.

(10) Patent No.: US 6,852,105 B2
(45) Date of Patent: Feb. 8, 2005

(54) METHOD AND APPARATUS FOR INSERTION OF SELF-DRAINING URINE APPARATUS INTO BLADDER

(75) Inventors: Magnus Bolmsjö, Lund (SE); Sonny Schelin, Rockneby (SE)

(73) Assignee: Prostalund Operations AB, Lund (SE)

( * ) Notice: Subject to any disclaimer, the term of this patent is extended or adjusted under 35 U.S.C. 154(b) by 0 days.

(21) Appl. No.: 10/630,118

(22) Filed: Jul. 30, 2003

(65) Prior Publication Data

US 2004/0059304 A1 Mar. 25, 2004

Related U.S. Application Data

(63) Continuation of application No. 10/415,616, filed on Apr. 28, 2003, which is a continuation-in-part of application No. 09/704,223, filed on Nov. 1, 2000, now Pat. No. 6,626,876.

(51) Int. Cl.$^7$ .......................... A61M 27/00; A61M 5/00
(52) U.S. Cl. .................... 604/544; 604/95.04; 604/104; 604/171
(58) Field of Search ................................. 604/544, 327, 604/517, 93.01, 95.04, 104, 171, 174, 524

(56) References Cited

U.S. PATENT DOCUMENTS

| | | | |
|---|---|---|---|
| 4,790,810 A | | 12/1988 | Pugh, Jr. et al. |
| 5,176,664 A | | 1/1993 | Weisman |
| 5,489,269 A | * | 2/1996 | Aldrich et al. ............ 604/95.04 |
| 5,738,654 A | | 4/1998 | Tihon |
| 5,941,849 A | * | 8/1999 | Amos et al. .............. 604/95.04 |
| 6,048,329 A | * | 4/2000 | Thompson et al. ....... 604/95.04 |
| 6,368,340 B2 | | 4/2002 | Malecki et al. |
| 6,524,268 B2 | * | 2/2003 | Hayner et al. ................ 604/8 |
| 6,626,876 B1 | * | 9/2003 | Bolmsjo et al. ............ 604/317 |
| 6,648,863 B2 | * | 11/2003 | Reever ........................ 604/327 |
| 6,656,146 B1 | * | 12/2003 | Clayman et al. ................ 604/8 |
| 2001/0049490 A1 | * | 12/2001 | Slanda et al. ............ 604/95.04 |
| 2002/0004644 A1 | * | 1/2002 | Koblish ..................... 604/104 |
| 2003/0191450 A1 | * | 10/2003 | Teague et al. .............. 604/524 |

* cited by examiner

*Primary Examiner*—Larry I. Schwartz
*Assistant Examiner*—Michael G. Bogart
(74) *Attorney, Agent, or Firm*—John R. Ley

(57) ABSTRACT

A device for the drainage of the bladder through the body's own urethra opening outside of the human body, comprising a tube-shaped body (10). The tube-shaped body is comprised: to assume a first contracted position and for taken up within the bladder as well as a to assume a second partially extended position. At least one thread (14) extends between the bladder and an opening of the urethra and is attached at a first end of the tube-shaped body so that the tube-shaped body can be extended from the first position to the second position during the application of a pulling force upon the thread. The tube-shaped body in the second partially extended position extends in such a manner so as to exceed the distance between the bladder and the point of the urethra's closing. The tube-shaped body is comprised in such a manner that it will return to the first position upon the release of the pulling force on the thread.

The device is inserted into the bladder, in that a tube-shaped body is extended and inserted into an extended tube-shaped introducing member. The introducing member is inserted in through the urethra, so that the end piece of the tube-shaped body enters the bladder. The tube-shaped body is pushed out of the tube-shaped introducing member and into the bladder during the course of which it returns to the first contracted position completely within the bladder and in the course of which the placement of a thread that is attached to the tube-shaped body and that extends outside of the urethra is left to remain.

33 Claims, 5 Drawing Sheets

METHOD AND APPARATUS FOR INSERTION OF SELF-DRAINING URINE APPARATUS INTO BLADDER

CROSS-REFERENCE TO RELATED INVENTIONS

This invention is a continuation of U.S. application Ser. No. 10/415,616 filed Apr. 28, 2003. U.S. application Ser. No. 10/415,616 is a continuation in part of U.S. application Ser. No. 09/704,223, filed Nov. 1, 2000, now Pat. No. 6,626,876 issued Sep. 30, 2003.

FIELD OF THE INVENTION

Prostate problems, such as benign prostate hyperplasia (BPH) or prostate cancer are usual occurrences among men. In many cases the symptoms experienced are very troublesome. Problems relating to the discharge of urine arise when the prostate gland swells to the extent that the urine duct, urethra, which runs through the prostate gland, is obstructed or pinched. The result of this process can lead to difficulties for the patient in being able to discharge urine at will, so-called urinary tract retention. Urinary tract retention can be either acute or chronic.

BACKGROUND OF THE INVENTION

The means for treating symptoms of urine retention is either surgery or another equivalent treatment, which removes the obstruction. Alternatively, the patient is required to have a catheter implanted or to learn so called self-draining. In the first case, a drainage catheter is placed into the urinary tract, from the penis and up into the bladder. The catheter is formed as a tube or a canal and is usually comprised of soft material, for example, latex, polyurethane, or silicone. At the end that lies in the bladder, the catheter is comprised of a balloon, which is blown up and prevents the catheter from slipping out. At the other end, outside of the penis, a clamp is usually attached so that the patient can open/close the catheter canal. Also urine can be collected by means of the attachment of a reservoir. The patient can also be taught to insert, on his own, a drainage catheter for him or herself into the bladder every time the urge to urinate arises and in that way can avoid the need to continually leave the catheter inside of him or herself.

There are a number of different forms of treatment with respect to obstruction by the prostate gland, such as surgery and treatment with heat. Aging problems in the form of acute urinary tract retention can arise, however, usually during a certain time after the treatment.

As relates to disease of the prostate, the type of assistance that is available today to many of those patients who have significant problems, and who no longer can rid themselves of urine spontaneously, is chronic catheter care in the form of continual use of a catheter. Alternatively, patients can be taught the technique of inserting an emptying catheter up through the urethra into the bladder every time the urge to urinate arises. However the patient must then always carry on his or her person sterile one-time use catheters. In certain more unusual cases, a stent can be placed into the prostate in order to stretch the tissue outward and allow the passage of urine. In the greatest majority of cases, however, a catheter is used. Disadvantages with all forms of catheter treatments, whether one uses an unremovable catheter or self-insertion, are that the patient's discomfort in using a catheter as well as the limitations on quality of life issues that come with it, i.e. socially, sexually, etc. In addition, there is a relatively high risk that urinary tract infections will arise through use of a catheter.

If the patient is determined to be an unsuitable subject to undergo a radical treatment of the disease by means such as surgery, due to weakness or other reasons use of a catheter will be required for the remainder of the patient's life.

Another usual form of treatment for obstructions caused by the enlargement of the prostate gland is by means of heat treatment using microwaves, radio waves, ultra sound or laser. The object of this type of treatment is to destroy a portion of the prostate tissue nearest to the urine through the urethra in order to achieve free passage of urine in this way. With such treatments, acute retention within the urinary tract usually arises. This is a result of the fact that the heat-treated prostate tissue becomes swollen. Thus, with respect to heat treatments, it is therefore quite usual that a catheter is inserted for approximately two weeks in order to insure the drainage of urine even during this period. Despite the fact that the drainage of urine is insured by using this method, the catheter in and of itself can result in problems for the patient.

SUMMARY OF THE INVENTION

One object of the present invention is to reduce the amount of displeasure experienced as a result of a patient's use of a catheter in association with the treatment of the prostate gland. Another object is to make possible the drainage of urine in association with other obstructions or another type of illness, for example, neurogenic bladder drainage disorders in women.

According to the invention there is introduced an elongated drainage body, such as a tube, a tube-shaped body, or a similar element that is coiled into one or more revolutions in the urine bladder in a first contracted position. The bends in the tube make it so that it cannot spontaneously slip out through the bladder neck. The tube is relatively soft so that it can be stretched out into an extended position if additional force is applied, and so that it will again assume its spiral shape if no outside force is applied. In the extended position it will function as a drainage catheter.

In one embodiment an elongated slit is formed in the elongated body to allow urine to leave the bladder and pass by the obstruction of the urethra. In one end of the body, a thread is attached. A free end of the thread runs out through the body's own urinary tract, which includes the urethra and penis/vagina. A small handle or stop can be made part of the thread in order to inhibit the end of the thread unintentionally receding into the urethra. In a second embodiment the elongated body is formed as a tube having a plurality of small perforations into which the urine can run.

When the patient experiences the urge to urinate, or for any other reason desires to empty the bladder, the patient pulls on the thread. The end of the body, which is attached to the thread is drawn down through the bladder, past the neck of the bladder and obstruction, and, in men, down through the prostate gland. The thread ought only be drawn to the extent that the end does not pass the apex of the prostate. Fittingly, a mark can be applied to the thread so that the treating doctor or nurse can designate how far the patient may draw so that the end will still remain inside of the prostate, yet will have passed the obstruction.

In such a manner, the patient can achieve drainage of the bladder. After drainage, the patient releases the thread, whereafter due to the spring mechanism or biasing force that is a result of the tube's winding spiral shape, the end will again be drawn in so that the entire tube lies in the bladder. The biasing force can be provided also by a stiffening wire attached to or embedded in the drainage body.

With the aid of the characteristics described in the invention, the tube is quite simple to apply, just as simple as inserting a normal drainage catheter.

It may be appropriate to provide the drainage body with a lubricating surface, so as to facilitate the insertion through the urethra. A preferred lubricating material is hydrogel but other materials with similar properties can be used.

As a result of the invention, a number of advantages are realized, among which are the following:

1. In the case that an obstruction that is hindering spontaneous emptying is of a temporary nature, for example after heat treatment, the patient himself will notice that he is again able to empty his bladder without means of assistance. He can then seek out medical assistance in order to remove the entire tube, or alternatively remove it himself.

2. The patient will experience a considerably lower degree of discomfort when he can avoid having a catheter inserted into the body or performing self-draining.

3. The risk of infection is likely to be considerably lower compared with catheter treatment.

4. The drainage will take place from within the bladder.

DETAILED DESCRIPTION OF PREFERRED EMBODIMENTS

Figure 1:
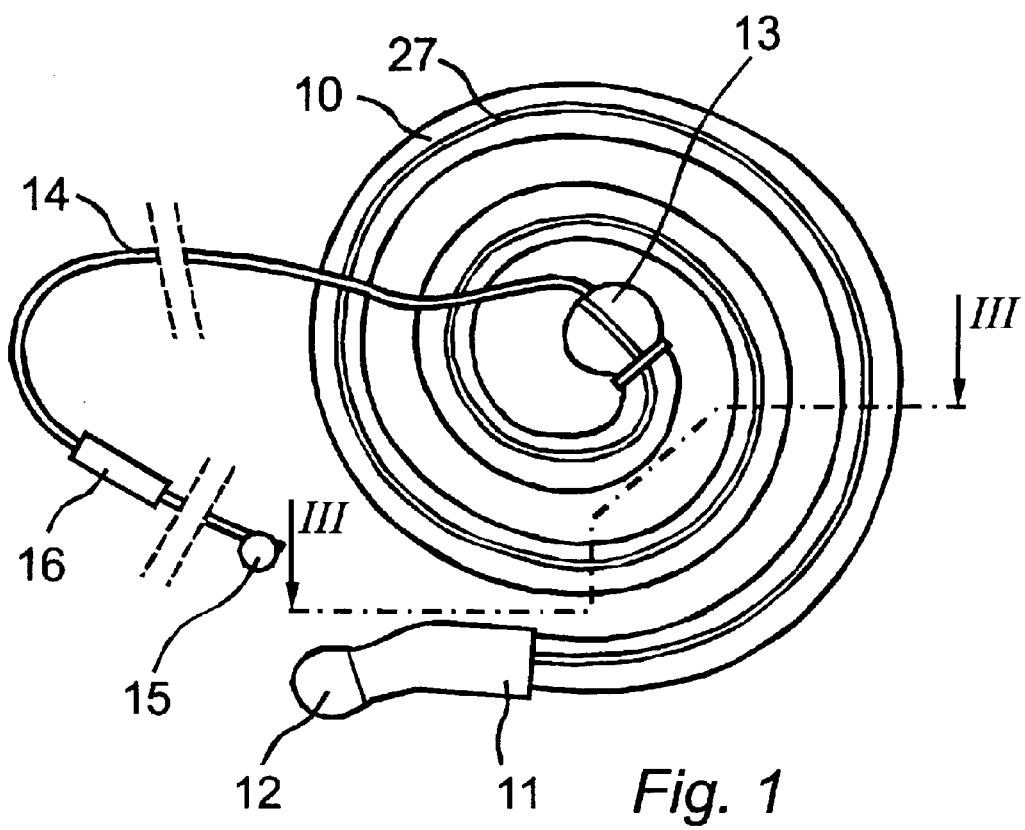
FIG. 1 shows a first embodiment of a device in accordance with the invention in a receding state.

In a first embodiment according to FIG. 1, an elongated body 10 functioning as a draining body has a first end that is attached with an end piece 11. The body 10 is formed as a flexible rod of silicon or polyurethane or a similar material and assumes, in one embodiment shown in FIG. 1, the drawn together, contracted or rolled-up form. The end piece 11 comprises a spherically formed ending 12, which makes possible the body's 10 introduction through the patient's urethra into the urine bladder. Through the application of a drawing pressure on the body 10, it can be caused to assume an extended form. A built in spring momentum, however, pulls the body 10 back to its contracted position when the pulling force is no longer applied.

In the embodiment shown in FIG. 1 the drainage body is formed with a slit 27 extending over a substantial part of the length of the drainage body. The slit 27 will allow urine to pass by the obstruction of the urethra when the drainage body 10 is in the extended position. This design of the drainage body can be manufactured in one step in a moulding process. By using silicon it is possible to produce the shape shown in FIG. 1 in one step, because it will release from the mould. Also other materials, such as polyurethane can be used. A stiffening wire (cf. FIG. 3) can be attached inside the slit 27 or be integrated with the drainage body, so as to achieve an appropriate stiffness and a property to return to the contracted position.

A second end of the body 10 is formed of a special elastic or soft section 13. The soft section 13 is connected to a first end of a thread 14. The thread 14 is sufficiently long such that it, along with the entire tube-shaped body 10 introduced into the urine bladder, stretches itself out of the urinary canal of the patient. The urinary canal of a male patient is comprised of the urethra and the penis and for a female patient, the urethra and the vagina, more specifically, the entire distance from the urine bladder to the respective body opening.

Figure 16:
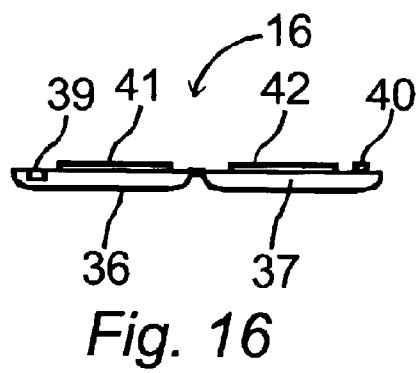
FIG. 16 is a schematic side elevational view of a marker for marking the position of the drainage body.
Figure 17:
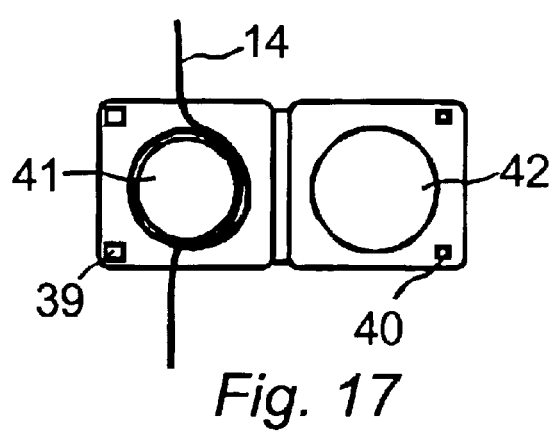
FIG. 17 is a plan view of the marker of FIG. 16.

At the thread's free end, there is a stop 15 in the form of a ball, or the like. After introduction of the body 10 into the urine bladder, the stop 15 prevents the thread from sliding into the urethra of the patient. A marker 16 on the thread makes it possible for the patient to control the drawing out of the thread 14 and body 10 to a suitable distance when used. An embodiment of the marker is shown in FIG. 16 and FIG. 17. Preferably the marker 16 is formed of a soft material. The use of the marker is described in more detail below as referenced in FIGS. 8–10.

Figure 2:
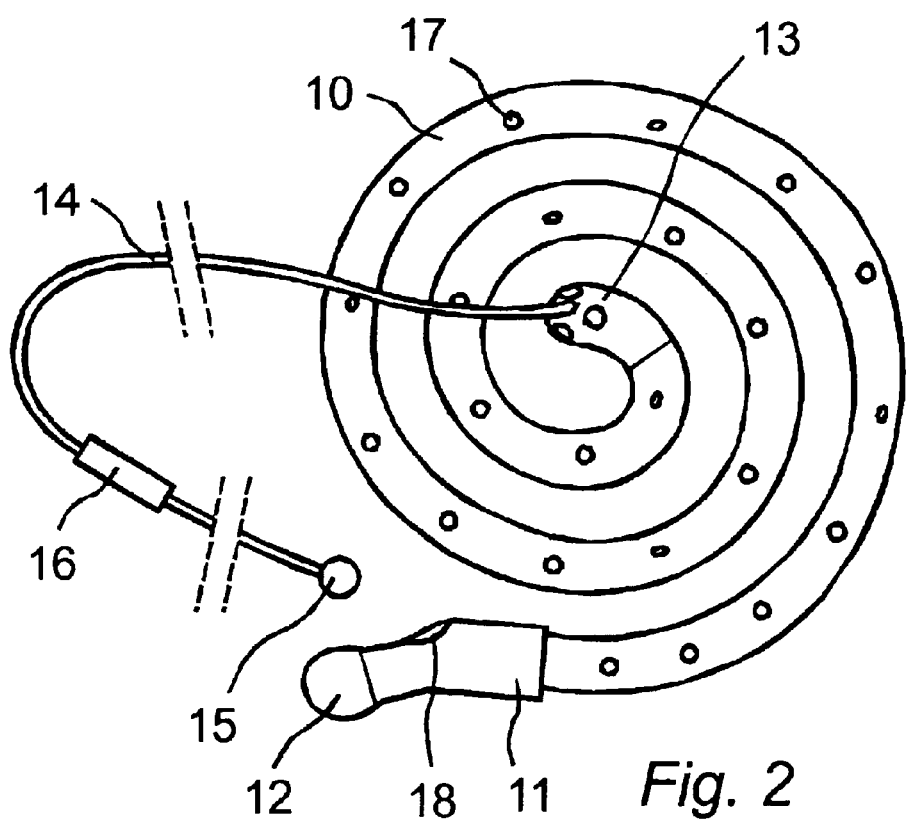
FIG. 2 shows a second embodiment of a device in accordance with the invention in a receding state.

In a second embodiment according to FIG. 2, a tube-shaped and extended body 10' has a first end that is attached with an end piece 11. The body 10' is formed as a flexible tube of polyurethane or similar material and assumes, in one embodiment shown in FIG. 2, the drawn together or rolled-up form. The end piece 11 is formed of a spherically formed ending 12, which makes possible the body's 10' introduction through the patient's urethra into the urine bladder. Through the application of a drawing pressure on the body 10', it can be caused to assume an extended form. A built in spring momentum, however, pulls the body 10' back to its contracted position when the pulling force is no longer applied.

The entire tube-shaped body is provided with a plurality of holes 17 that allows for the urine to run into the body's hollow inner space. The holes 17 are accordingly evenly distributed and are of such size that the risk of occlusion is small. A larger opening 18 is provided in the end piece 11 for the drainage of the urine bladder in association with the introduction of the body therein.

Figure 3:
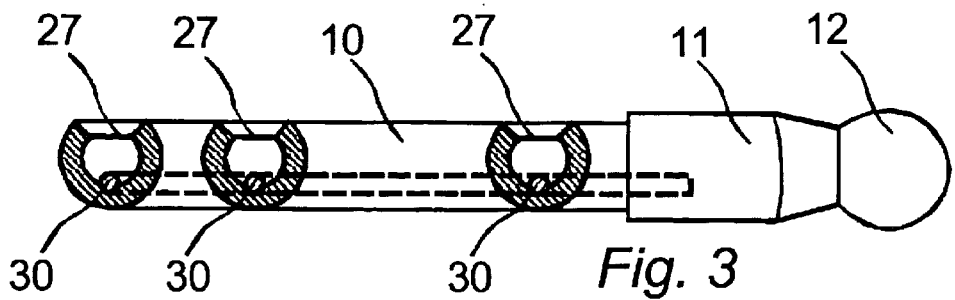
FIG. 3 is a sectional view from line III—III of the device in FIG. 1.
Figure 12:
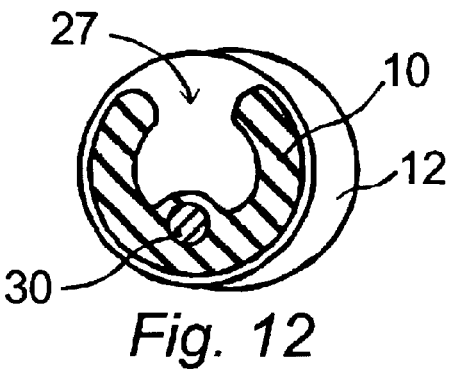
FIG. 12 is a cross sectional view of a first alternative embodiment of the device in accordance with the invention.
Figure 13:
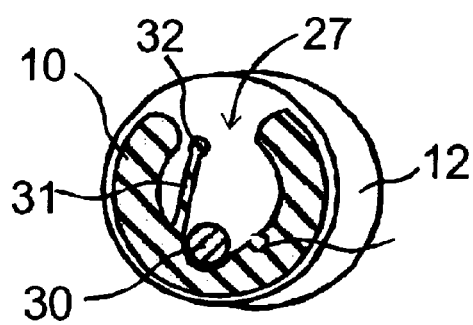
FIG. 13 is a cross sectional view of a second alternative embodiment of the device in accordance with the invention in a first position.
Figure 14:
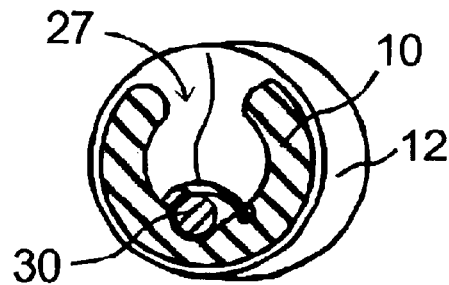
FIG. 14 is a cross sectional view of the device in FIG. 13 in a second position.

FIG. 3 is a sectional view of the device 10 shown in FIG. 1. The end piece 11 and the ending 12 are formed to facilitate the insertion of the device in the urethra and the bladder. The slit 27 will allow urine to enter the tube-shaped body when the device 10 is partly or completely within the bladder. A stiffening wire 30 is attached to or embedded in the drainage body. The stiffening wire will provide the device with an appropriate stiffness that will ensure that the device regains its contracted position after being extended. It is also possible to produce the drainage body from a material that will provide an appropriate stiffness without the stiffening wire. Other embodiments of the stiffening wire 30 are shown in FIG. 12 to FIG. 14. Preferably the stiffening wire 30 is inserted in and securely attached to the end piece 11 as shown in dashed lines.

The shape of the device can be accomplished in a one step moulding process if a suitable material such as silicone is used. Silicone will allow a negative angle on the forming tool because the adhesive forces are very low. The costs for producing the device by this method thus are very low.

Figure 4:
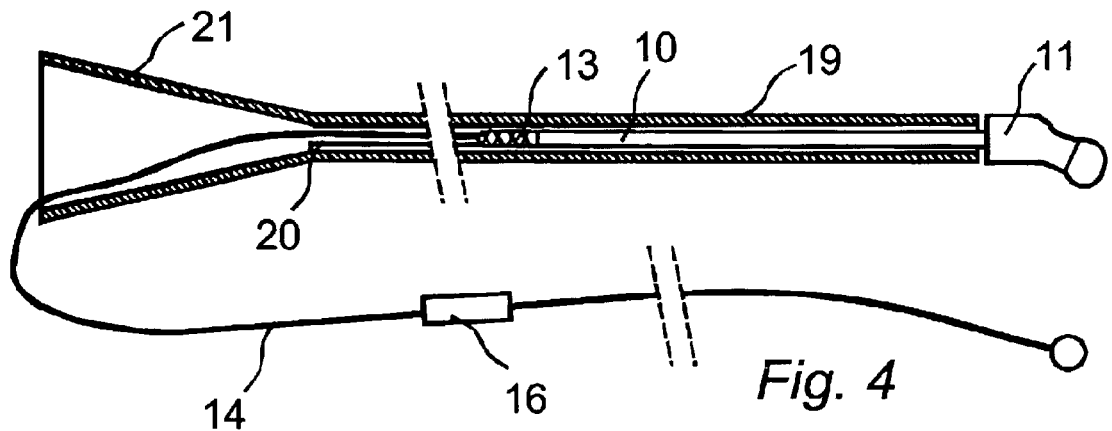
FIG. 4 shows the device in FIG. 2 in an extended state and introduced into an introducing member.

FIG. 4 depicts an introducing member 19. In the embodiment shown, the introducing member 19 is comprised of a flexible tube that is open at both ends. Accordingly, the introducing member 19 is comprised of polyurethane, polyethylene or a similar material. One end of the introducing member 19 comprises a conical part 21 for the purpose of making possible the introduction of a driving element (see description of FIG. 5). The conical part can also comprise a gripping means for the doctor or nurse who is using the device. In the center of the introducing member near the conical part, a guide thread 20 is attached. The guide thread 20 runs through the introducing member and makes it possible to eject the body 10 that has been placed within the introducing member 19.

In FIG. 4, the tube-shaped body 10 is introduced into the introducing member 19 and thereby extended to assume a second position. The insertion of the tube-shaped body 10 can be facilitated by the application of a thin layer of lubricating material such as a hydrogel. When water is applied the hydrogel layer will provide a very low friction. However, in its original state outside of the introducing member 19, the body 10 will attempt to reassume the shape as described in FIG. 2. The soft section 13 of the body 10 is positioned within the introducing member 19 so that it is turned against the conical part 21 while the end piece 11 extends outside of the introducing member 19. In this way the introducing member 19 and the tube-shaped body 10 together form a device that can be inserted through the urethra. The end piece 11 and the spherically formed ending 12 have a shape that will facilitate the insertion of the device through the urethra.

Figure 5:
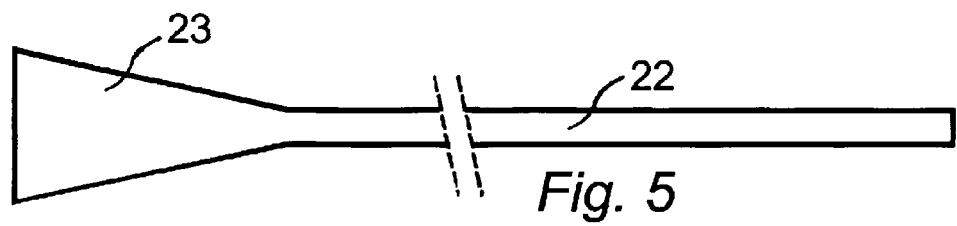
FIG. 5 shows a driving element that can be used to push the device in FIG. 2 out of the introducing member.

FIG. 5 displays one embodiment of a driving element 22. Preferably the driving element 22 is comprised of a conical section 23 corresponding to the conical part 21 of the introducing member 19. Also in this embodiment the conical section 23 can be used as a gripping means. The driving element 22 can also be formed from polyurethane or a material with similar properties.

Figure 6:
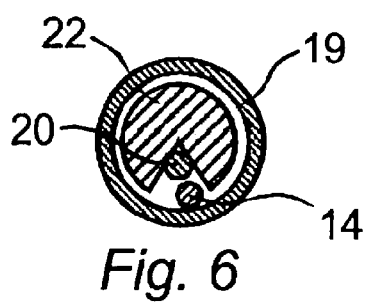
FIG. 6 is a cross-sectional view of the introducing member in FIG. 4 containing an already introduced first embodiment of a driving element.

FIG. 6 is a cross-sectional view, which shows the introducing member 19 wherein a first embodiment of the driving element 22 has been introduced. The driving element 22 has a circular cross-section with a receding slit for receiving a guide thread 20 and the thread 14. The driving element 22 is placed into the introducing member 19 when the introducing member is in the desired position with the end piece inserted into the bladder and with the driving element 22 pressing the tube-shaped body 10 into the urine bladder.

Figure 7:
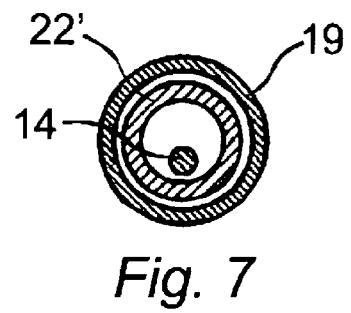
FIG. 7 is a cross sectional view of the introducing member in FIG. 4 containing an already introduced second embodiment of a driving element.

FIG. 7 is a cross sectional view, which shows the introducing member 19 along with an alternative and preferred embodiment of a driving element 22' introduced therein. The alternative driving element 22' is tube-shaped with a central inner cavity created for the purpose of drawing through it the thread 14. The guide thread 20 is not present in the embodiment shown according to FIG. 7 and is not required.

Prior to insertion, the thread 14 is drawn through the introducing member 19 so that the thread extends outwardly into the rear conical part 21. The thread also extends through the driving element 22, 22', so as to be available from the exterior. Thereafter the user pulls on the thread 14 so that the whole body 10, with the exception of the end piece 11, is drawn into the introducing member 19. If a guide thread 20 is used, the body 10 will follow the guide thread 20 and its position will be stretched out accordingly. The end piece 11 is preferably formed with the same outer diameter as the introducing member 19. As a final aspect of the preparation for the introduction, the driving element 22, 22' is guided into the introducing member 19 from its end possessing the conical part 21 until the driving element 22, 22' lies against the soft section 13 of the body 10. The introduction of the driving element 22, 22' can also be postponed to a later time.

In the above-described embodiment, the entire device is inserted in its full length through the urethra and up into the bladder. The introducing member 19 should also be of such length so that the end piece is ensured of being introduced into the urine bladder. In a simple manner, the end piece's position can be monitored by the fact that urine drains from the introducing member 19. The driving element 22 can therewith be drawn out of the introducing member 19, or be provided with channels running along its surface for the purpose of drawing away urine when the driving element 22 is inserted into the introducing member 19.

After ensuring that the end piece is correctly positioned, the full-length of the driving element 22, 22' is inserted into the introducing member 19, wherewith the body 10 passes into the bladder and assumes its contracted form. Thereafter the driving element 22, 22' along with the introducing member 19 are drawn completely out of the urethra. During removal of the driving element 22, 22' and the introducing member 19, the thread 14 should not be placed under any pressure, but should slide out freely through and from the introducing member 19 and the driving element 22'.

Figure 8:
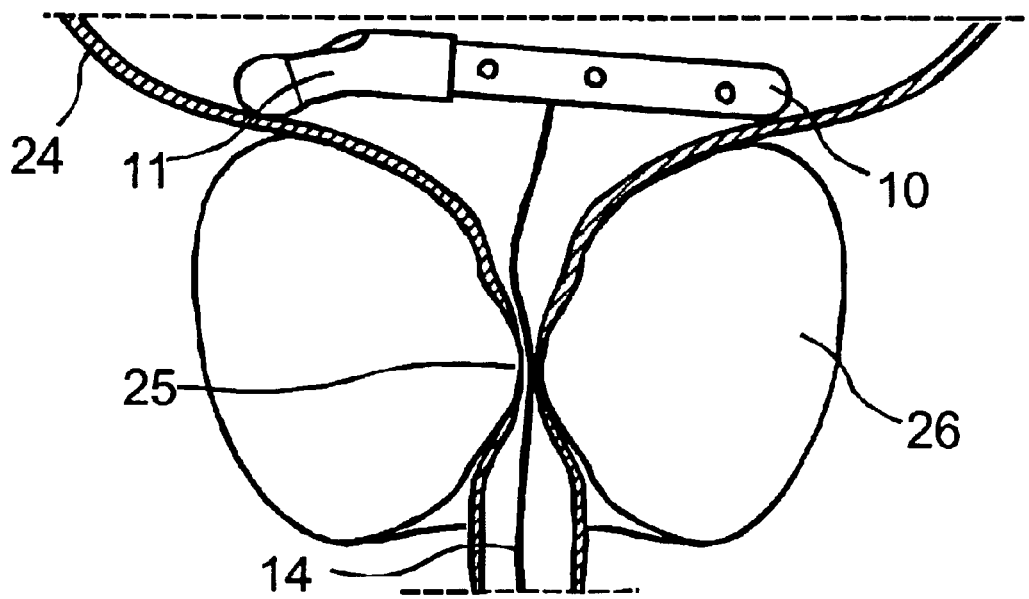
FIG. 8 shows a schematic view of the device in FIG. 2 fully introduced into a urine bladder.

FIG. 8 is a schematical view of the body 10' as introduced into the bladder 24 and with its end piece 11 resting against the urine bladder's wall. The thread 14 runs down through the point of the urethra's closing 25 and is accessible outside of the body. The point of the urethra's closing 25 is, as in the drawing provided, caused by the prostate tissue 26 that has been enlarged.

Figure 9:
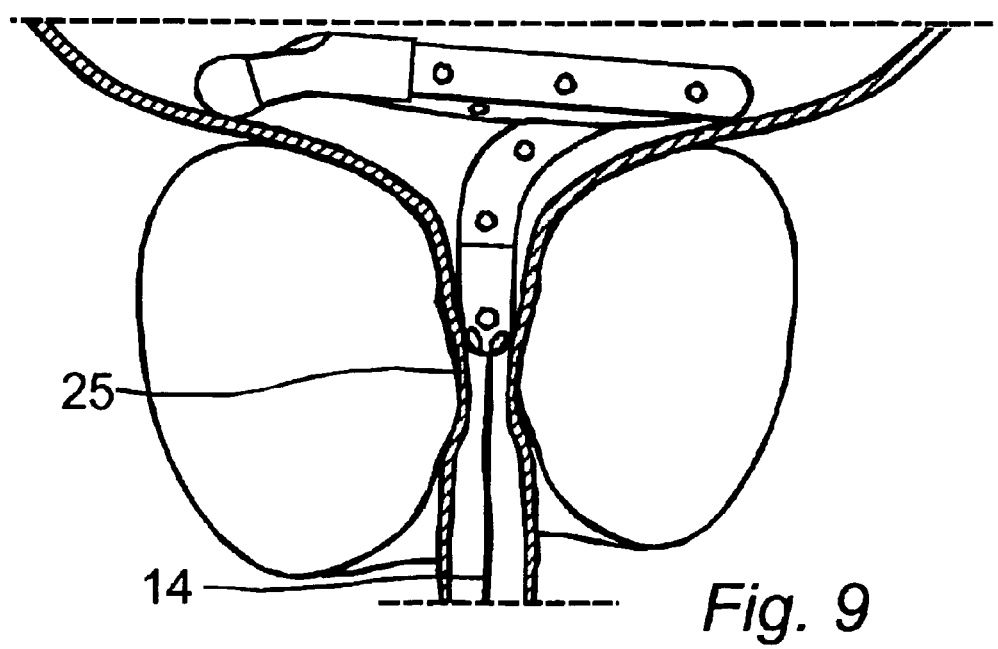
FIG. 9 shows the device in FIG. 8 extended to a first position partially drawn down into the urethra.
Figure 10:
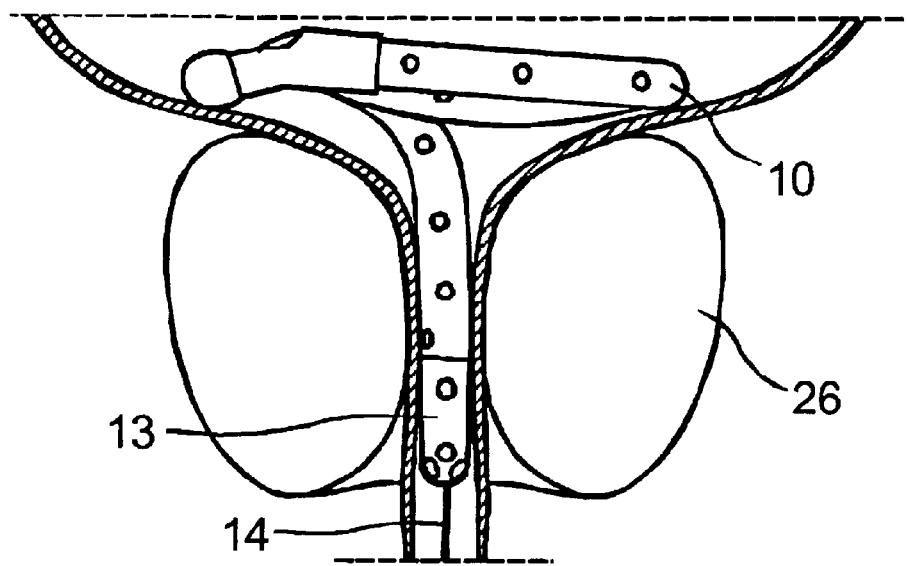
FIG. 10 shows the device in FIG. 8 extended to a second position drawn down into the urethra into such a position that the urine can freely flow out of the urine bladder.

When the urge to urinate arises or during other drainage of the bladder, the patient draws the thread 14, whereafter conditions in accordance with FIG. 9 will arise. The soft section 13 has been drawn down through the neck of the bladder and presses down upon tissue that is blocking the urethra when force is applied to the thread 14.

Additional drawing on the thread 14 results in the body 10' being drawn down through the prostate 26 and creates a canal, through which the patient can empty his bladder. These circumstances are exhibited in FIG. 10, where the soft section 13 has been completely drawn past the point of the urethra's closing 25. Urine can then freely pass through the tube-shaped body 10'. After drainage has occurred the thread 14 is released wherewith the body 10' slowly returns to the contracted position shown in FIG. 1, FIG. 2 and FIG. 8.

If the condition which has caused the point of the urethra's closing 25 abates, for example after a certain time subsequent to heat treatment of the prostate, the entire device can be removed by the patient simply drawing out the entire thread 14. The body 10' will then follow in the same path of removal without damaging the urethra or other tissue.

In addition to polyurethane other similar pliable materials can be used to form the tube-shaped body 10', the introducing member 19, and the driving element 22, 22'. An example of such material is silicone. The introducing member 19, however, should have a certain rigidity so that the tube-shaped body can be safely pushed through it.

Figure 11:
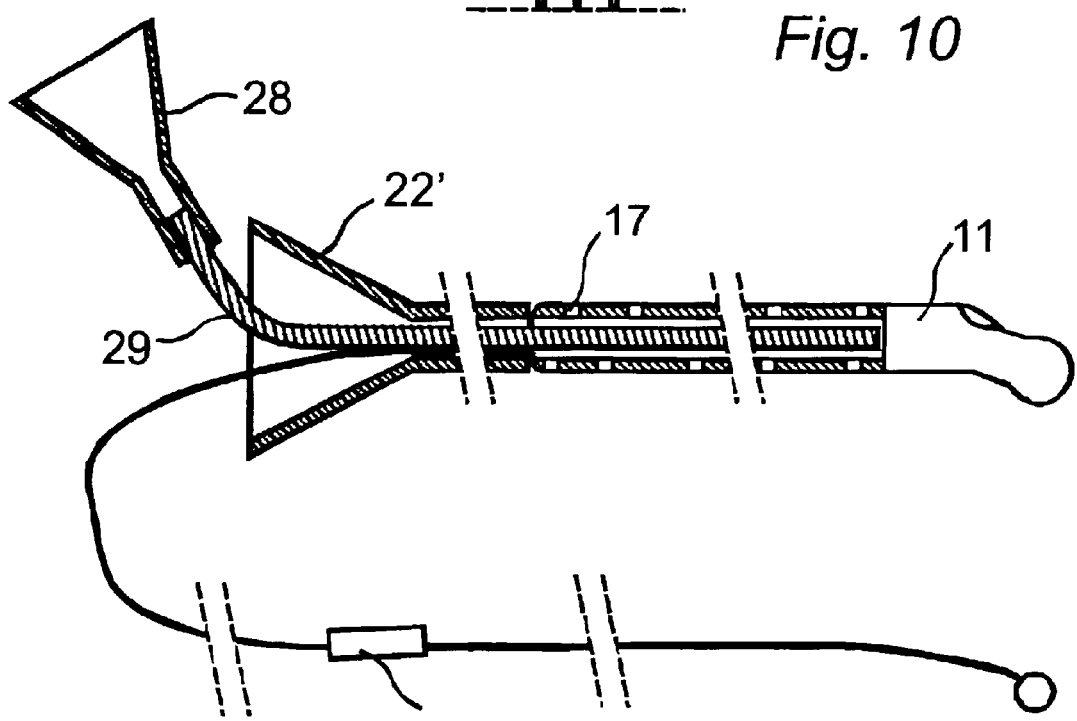
FIG. 11 is a schematic view drawing of an alternative embodiment of an introducing member.

In the embodiment according to FIG. 11, the introducing member is comprised so that a flexible guide thread 29 has an outer dimension less than the diameter of the tube-shaped body's 10 inner diameter. In order to facilitate the use of the introducing member, the thread 29 is provided with a gripping means 28. In the exhibited embodiment, a circular cross-section is used. The driving element 22' also in this embodiment is tube-shaped.

In the embodiment shown in FIG. 11 the driving element 22', like the entirety of the tube-shaped body 10, is guided via the flexible guide thread 29. Accordingly, the flexible guide thread 29 is extended throughout essentially the entirety of the tube-shaped body 10. One advantage of this embodiment is that the tube-shaped body 10 can be created to possess a greater outer diameter and therewith offer enhanced drainage capacities. The flexible guide thread 29 can be comprised of a spun or wound piano wire or a similar material and should be sufficiently rigid so that the tube-shaped body 10 remains in the second extended position when it is moved over the guide thread 29.

FIG. 12 shows a first embodiment of the drainage body 10. A slit 27 is formed along the body to allow urine to enter a longitudinally extending cavity within the body and to escape there through. The spherically formed ending 12 is partly shown. In the embodiment shown in FIG. 12 the stiffening wire 30 is embedded in the body 10. The stiffening wire 30 preferably should not be in a direct contact with urine.

In the alternative embodiment shown in FIG. 13 and FIG. 14 the stiffening wire 30 extends in a recess in the bottom of a longitudinally extending cavity within the body. A tongue 31 having a spherically formed tip 32 extends from an inner surface of the body 10. After insertion of the stiffening wire 30 into the recess the tongue 31 is bent over the wire 30 and pressed down into a recess 33. The recess is formed to receive and to retain the tip 32 of the tongue as shown in FIG. 14.

Figure 15:
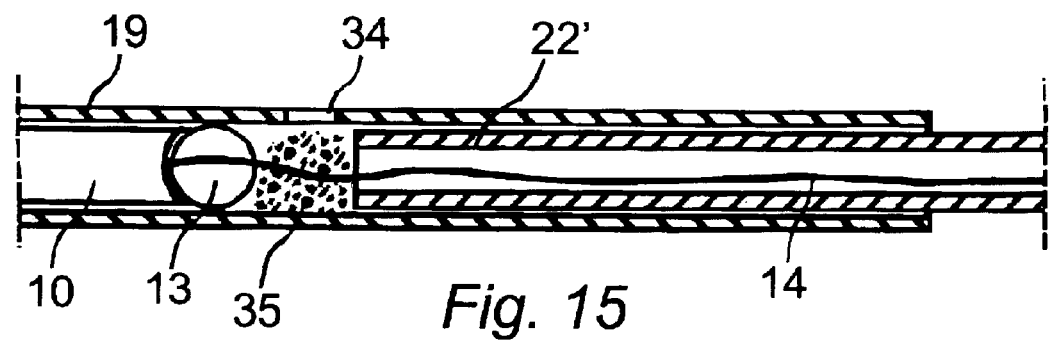
FIG. 15 shows schematically injection of a lubricant into an introducing member.

FIG. 15 shows a section of the introducing member 19 and the elongated body 10 with the soft spherical end 13 inserted therein. The driving element 22' is also inserted in the introducing member 19, a small space being left between the elongated body 10 and the driving element 22'. When the driving element 22' is advanced through the introducing member 19 it may be appropriate to facilitate the movement. An aperture 34 is formed in the introducing member 19 to allow the introduction of a lubricant 35 to the interior of the introducing member 19.

In the embodiment shown in FIG. 16 and FIG. 17 a first bowl shaped element 36 and a second bowl shaped element 37 connected by a hinge section 38 form the marker 16. A snap lock mechanism is formed by indentations 39 in the first bowl shaped element 36 and protruding elements 40 on the second bowl shaped element 37. A first cylindrical member 41 on the first bowl shaped element 36 is used to wind the thread 14 up, and a second cylindrical member 42 on the second bowl shaped element 37 will lock the thread in position when the two bowl shaped elements are pressed together.

The invention claimed is:

1. A method for inserting a drainage body into the bladder, wherein the drainage body is formed so as to assume a first contracted position when taken up within the bladder, the drainage body is formed so as to assume a second partially extended position, a thread having a length sufficient to extend between at least the bladder and an opening of the urethra and being connected with a first end of the drainage body for the purpose of extending the drainage body from the first position to the second position extending into the urethra upon the exertion of a pulling force upon the thread, a drainage channel of the drainage body in the second partially extended position has a length which exceeds the distance between the bladder and the point of a closing or an obstruction of the urethra; and the drainage body is formed in such a manner that it returns to the first position upon the release of the pulling force on the thread, said method including the steps of inserting the drainage body into a hollow introducing member, leaving an end piece of the drainage body having a rounded ending form extending from the introducing member, inserting the introducing member into the urethra to a position where the end piece is received in the bladder, and pushing the drainage body into the bladder.

2. A method for the insertion of a device for the drainage of the bladder through the body's own urethra opening outside of the human body, wherein a urine drainage body extends from a first contracted position to an extended second position and is inserted in the second position into an elongated tube-shaped introducing member, the tube-shaped introducing member is inserted through the urethra, so that an end piece of the body passes into the bladder, the body is pushed out of the tube-shaped introducing member and into the bladder during the course of which the body returns to the first contracted position completely within the bladder and in the course of which the placement of a thread that is attached to the body extends outside of the urethra.

3. A method as defined in claim 2, wherein:

the urine drainage body comprises a tube-shaped body.

4. An introducing apparatus for the insertion of an elongated urine drainage apparatus into a bladder, the drainage apparatus comprising a body that has a first contracted position and a second extended position and a thread attached to one end, the introducing apparatus comprising:

an introducing member has a length sufficient to extend from an exterior opening of a urinary canal through the urinary canal to the bladder;

the introducing member has a transverse dimension to fit within the urinary canal from the exterior opening of the urinary canal to the bladder neck; and the introducing member defines a cavity extending entirely along the length of the introducing member, the cavity having a transverse dimension to receive the urine drainage body therein when the body is in the extended position.

5. An introducing apparatus according to claim 4, further comprising:
a driving element for inserting into the introducing member to push the body from the introducing member into the bladder, the driving element having a transverse dimension to fit within the cavity of the introducing member and having a length sufficient to extend at least most of the way through the cavity.

6. An introducing apparatus according to claim 5, wherein:
the introducing member comprises a conical part at one end to facilitate the insertion of the driving element into the introducing member.

7. An introducing apparatus according to claim 6, wherein:
the driving element comprises a conical section at one end that engages the conical part of the introducing member when the driving element is fully inserted within the introducing member.

8. An introducing apparatus according to claim 5, wherein:
the driving element comprises a circular cross section with a receding slit for receiving the thread when the driving element is inserted into the introducing member.

9. An apparatus according to claim 8, the comprising an elongated slit, wherein:
the introducing member comprises a guide thread that is attached to the introducing member and runs through the introducing member cavity to engage the elongated slit in the body and guide the body into and out of the introducing member.

10. An introducing apparatus according to claim 5, wherein:
the driving element defines an inner cavity for receiving the thread when the driving element is inserted into the introducing member.

11. An introducing apparatus according to claim 4, the drainage apparatus comprises an end piece connected to the body, wherein:
the introducing member has a transverse dimension that is essentially the same as the transverse dimension of the end piece and the introducing member fits adjacent to the end piece when the body is inserted into the introducing member.

12. An introducing apparatus according to claim 4, wherein:
the introducing member has an aperture to the cavity between its ends to insert lubricant into the cavity.

13. An introducing apparatus for the insertion of an elongated urine drainage apparatus into a bladder, the drainage apparatus comprising a tube shaped body that has a first contracted position and a second extended position and a thread attached to one end, the introducing apparatus comprising:
a flexible guide that has a length sufficient to extend from an exterior opening of a urinary canal through the urinary canal to the bladder; and
the flexible guide has a transverse dimension to fit within the tube shaped body when the body is in the extended position; and
the flexible guide has sufficient rigidity to temporarily hold the tube shaped body in the extended position when the flexible guide is inserted in the body.

14. An introducing apparatus according to claim 13, wherein:
the flexible guide comprises a grip at one end to facilitate the insertion of the drainage apparatus through the urinary canal.

15. An introducing apparatus for the insertion of an elongated urine drainage apparatus into a bladder, the drainage apparatus comprising a tube shaped body that has a first contracted position and a second extended position and a thread attached to one end of the body, the introducing apparatus comprising:
a flexible guide that has a length sufficient to extend from an exterior opening of a urinary canal through the urinary canal to the bladder;
the flexible guide has a transverse dimension to fit within the tube shaped body when the body is in the extended position; and
the flexible guide has sufficient rigidity to temporarily hold the tube shaped body in the extended position when the flexible guide is inserted in the body;
a driving element defining an inner cavity for inserting onto the flexible guide to push the urine draining body from the flexible guide into the bladder;
the driving element has an interior transverse dimension that is larger than the transverse dimension of the flexible guide;
the driving element has a exterior transverse dimension to fit within the urinary canal from the exterior opening of the urinary canal to the bladder neck; and
the driving element has a length sufficient to extend from an exterior opening of a urinary canal through the urinary canal to the bladder.

16. An introducing apparatus according to claim 15, wherein:
the driving element comprises a conical section at one end.

17. A method for inserting an elongated urine drainage apparatus into a bladder, the drainage apparatus comprising a body that has a first contracted position and a second extended position and a thread attached to one end, the method comprising:
inserting the drainage body into a cavity in an introducing member thereby extending the drainage body;
inserting the introducing member and drainage apparatus through a urethra to the bladder;
pushing the drainage apparatus out of the introducing member and into the bladder;
removing the introducing member from the urethra while leaving the drainage apparatus in the bladder.

18. A method as defined in claim 17, further comprising:
extending the thread through the introducing member cavity so that part of the thread remains outside of the urethra when the introducing member and drainage apparatus are inserted through the urethra.

19. A method as defined in claim 17, further comprising:
inserting the drainage body into the introducing member cavity by pulling the thread through the cavity.

20. A method as defined in claim 17, further comprising:
pushing the drainage apparatus with a driving element.

21. A method as defined in claim 20, further comprising:
engaging a conical part of the introducing member with a conical section of the driving element when the drainage apparatus is pushed out of the introducing member.

22. A method as defined in claim 20, further comprising: lubricating the driving element.

23. A method as defined in claim 17, further comprising: lubricating the introducing member.

24. A method as defined in claim 17, further comprising: lubricating the drainage apparatus.

25. A method as defined in claim 17, further comprising: lubricating the cavity of the introducing member through an aperture between the ends of the introducing member.

26. A method as defined in claim 17, further comprising: guiding the drainage body into the introducing member with a guide thread in the cavity of the introducing member.

27. A method as defined in claim 17, further comprising: inserting the introducing member and drainage apparatus through a urethra until urine flows through the introducing member from the bladder.

28. A method as defined in claim 17, the drainage apparatus comprising an end piece, the method further comprising:

inserting the drainage body into the cavity; and moving the end piece adjacent to the introducing member.

29. A method as defined in claim 28, further comprising: guiding the introducing member through the urethra with the end piece.

30. A method for inserting an elongated urine drainage apparatus into a bladder, the drainage apparatus comprising a tube shaped body that has a first contracted position and a second extended position and a thread attached to one end, the method comprising:

inserting a flexible guide into the tube shaped body;

holding the tube shaped body in the second position with the flexible guide;

extending the flexible guide from an exterior opening of a urinary canal through the urinary canal to the bladder;

inserting the flexible guide and drainage apparatus through the urethra to the bladder;

pushing the drainage apparatus from the flexible guide and into the bladder;

removing the flexible guide from the urethra while leaving the drainage apparatus in the bladder.

31. A method as defined in claim 30, further comprising: pushing the drainage apparatus from the flexible guide with a driving element.

32. A method as defined in claim 30, further comprising: lubricating the drainage apparatus.

33. A method as defined in claim 30, the drainage apparatus comprising an end piece, the method further comprising:

guiding the drainage apparatus and flexible guide through the urethra with the end piece.

* * * * *